United States Patent

Johansson et al.

Patent Number: 5,427,631
Date of Patent: Jun. 27, 1995

[54] PROSTHETIC ARTICLES MADE OF SURFACE CONVERSION NITRIDED TITANIUM OR TITANIUM ALLOYS

[75] Inventors: Erik Johansson; Helena Westberg, both of Uppsala, Sweden

[73] Assignee: Ytbolaget I Uppsala Aktiebolag, Uppsala, Sweden

[21] Appl. No.: 219,920

[22] Filed: Mar. 30, 1994

Related U.S. Application Data

[62] Division of Ser. No. 672,908, Mar. 21, 1991, Pat. No. 5,320,686.

[30] Foreign Application Priority Data

Mar. 21, 1990 [SE] Sweden ............... 9001009

[51] Int. Cl.[6] .............. C22C 14/00; C21D 9/00
[52] U.S. Cl. .................. 148/23.8; 148/537; 427/248.1; 427/250
[58] Field of Search ............ 148/238, 537; 427/250, 427/248.1

[56] References Cited

U.S. PATENT DOCUMENTS

| | | | |
|---|---|---|---|
| 3,643,658 | 2/1972 | Steinemenan | 148/6.3 |
| 4,511,411 | 4/1985 | Brunner et al. | 148/20.3 |
| 4,693,760 | 9/1987 | Sioshansi | 148/239 |
| 4,790,851 | 12/1988 | Suire et al. | 623/16 |
| 5,152,774 | 10/1992 | Schroeder | 427/2 |
| 5,152,794 | 10/1992 | Davidson | 623/16 |
| 5,192,323 | 3/1993 | Shetty et al. | 623/16 |

OTHER PUBLICATIONS

Dion et al Biomaterials vol. 14(3) (Feb. 1993) 169.
Johansson et al Jour. Mat. Sc.: Mat. in Medicine, 4 (1993) 132.
Raveh et al Thin Solid Films 186 (1990) 241.
Grill et al Surf. & Coat. Tech. 43/4 (1990) 745.
Peterson et al Jour. Biomed. Mat. Res. 22 (1988) 887.
Metin et al Met. Trans. 20A (1989) 1819.
Konuma et al Jour. Less-Comm. Metals 52 (1977) 145.
Dion et al Biomaterials, 14(9) (Jul. 1993) 712.

*Primary Examiner*—Upendra Roy
*Attorney, Agent, or Firm*—Dennison, Meserole, Pollack & Scheiner

[57] ABSTRACT

Objects of titanium or titanium alloys having the surface converted to a hard and wear-resistant nitride layer with good adhesion, which is distributed uniformly and also provides internal capillaries. The objects are produced by being treated in a vacuum furnace with an atmosphere of pure nitrogen gas at a temperature of 650°–1000° C. and at a pressure below atmospheric pressure. The thickness of the nitride layer can be controlled by controlling the treatment time and temperature.

4 Claims, 4 Drawing Sheets

PROSTHETIC ARTICLES MADE OF SURFACE CONVERSION NITRIDED TITANIUM OR TITANIUM ALLOYS

This is a divisional of application Ser. No. 07/672,908, filed Mar. 21, 1991, now U.S. Pat. No. 5,320,686.

BACKGROUND OF THE INVENTION

1. Field of the Invention

The invention relates to products manufactured from titanium and/or titanium alloys having a hard, wear-resistant and pure nitride layer in the surface, and to a method of manufacturing such products.

Titanium and its alloys are used primarily in corrosive environments and in applications demanding a combination of good strength properties (ultimate stress limit, elasticity module, ductility) and low density. Titanium and titanium are generally used in this connection in the aviation industry. Thanks to the unique corrosion and biocompatibility properties of titanium, it is also used to make prostheses, e.g. parts for cardiac valves, load-carrying hip and knee joints, etc. Other areas requiring the unique corrosion resistance of titanium are in the biotechnical and chemical industries, where titanium and titanium alloys are used primarily for the material in valves and pump cylinders which are subjected to high pressure in combination with sliding contact and extremely high tightness requirements at the sliding surface. According to the present invention a nitride layer is formed on titanium or titanium alloys by means of surface conversion, this layer having extremely good friction, corrosion and biocompatibility properties, as well as extremely good adhesion to the substrate. Capillaries and the like are also provided with the nitride layer, The invention relates to products such as prosthesis shafts, wear-parts for prosthesis shafts, as well as valve parts and pump cylinders, manufactured out of titanium or titanium alloys, with a pure nitride layer of this type in the surface. The invention also relates to a method of manufacturing such products.

The purpose of the nitride layer is to improve wear, corrosion and friction properties in the surface of titanium or its alloys. This nitride layer improves the corrosion-proof and biocompatibility properties of the titanium or titanium alloy.

2. DESCRIPTION OF RELATED ART

Several methods are already known to harden the surface of titanium and titanium objects. It is, for instance, known to oxide the surface of titanium by heating so that oxygen in the air combines with the titanium to give $TiO_2$ and forming an oxide layer. However, this oxide layer is neither very hard nor very thick and its properties are too poor for the applications mentioned above. Another way of hardening the surface of titanium objects is to immerse them in a cyanide-based salt melt at a temperature of about 800° C. This treatment results in a mixed zone comprising nitrogen, carbon and a small proportion of oxygen. The thickness of the layer is about 0.035 mm at a hardness 700 HV at the edge. This is the known Tiduran process according to Degussa, The method does not produce pure nitride since both oxygen and carbon are present, The corrosion and biocompatibility properties, as well as mechanical properties, hardness and adhesion to the substrate thus deteriorate.

The known ionic nitration is performed at treatment temperatures of 400° C. to 600° C. With the aid of abnormal corona discharge, nitrogen is created in ionized form and is included in the surfaces of the workpiece. The hardness values at the surface reach about 1500 HV. However, difficulties arise when treating the interior of workpieces, since the method is a so-called "line-of-fire process", and treating spherical surfaces or the like (e.g. joint prostheses), Using the PVD (Physical Vapour Deposition) technique a surface layer of titanium nitride can be obtained. The PVD concept covers a large number of coating processes. However, two main principles can be distinguished: vaporization and sputtering. In the case of vaporization the coating material is heated in a vacuum chamber to a temperature at which vaporization occurs. Heating may be performed resistively, inductively or by irradiation with laser or electrons. The component to be coated is placed in the same chamber as the vaporization source. Since vaporization occurs under vacuum ($10^{-2}-10^{-4}$ Pa), the vaporized atoms will move undisturbed in straight paths from the source to the surface of the component, where they are adsorbed and form small crystal cores which in time grow into a coating. In the case of sputtering the coating material is in the form of a solid plate which is placed on a negative potential (ca.1kV) in a vacuum chamber. The component to be coated is placed on earth and, when a vacuum has been achieved ($10^{-3}$ Pa), argon gas is leaked into the chamber to a pressure in the vicinity of 1 Pa. This produces a corona discharge in the gas, whereupon the argon atoms are ionized to positive argon ions and are accelerated towards the cathode (usually known as the target). When the argon ions encounter the target they will, by resilient impact dislodge the target atoms from the cathode plate. This is termed sputtering. The target atoms thus sputtered from the surface will travel through the chamber until they land on a surface and a coating is produced. All PVD methods are line-of-fire processes and internal coating of capillaries, for instance, is thus impossible and even coating bodies of spherical or similar shape is difficult. Furthermore, no chemical reaction occurs between the layer and the basic material and adhesion of the surface layer may therefore be poor. A layer is formed by deposition with this method.

Using the CVD (Chemical Vapour Deposition) method titanium nitride can be precipitated at increased temperature from a gas mixture, usually consisting of titanium tetrachloride, hydrogen and nitrogen (or some other nitrogen component, such as ammonia). In this process a chemical reaction is activated thermally, usually in a furnace. A gas mixture is conveyed to a reactor and a solid phase is deposited in the form of a surface coating on the heated object. Surface irregularities are covered very well in this method. However, in certain cases the method may give rise to poorer adhesion of the nitride layer due to the formation of chloride salts in the boundary layer between then titanium and the titanium nitride. With this method also, the layer is formed by deposition.

It is known that titanium and titanium alloys that are subjected to an atmosphere containing hydrogen at increased temperature very easily give hydrogen embrittlement, resulting in greatly deteriorated mechanical properties of both layer and substrate.

In the case of ion implantation a surface is irradiated with high-energy ions which penetrate into and alter the composition of the surface layer, and often also its structure. Modern equipment for ion implantation enables the implantation of sufficiently large doses within a reasonable time so that with certain combinations of ion type and substrate material a certain improvement is obtained with respect to friction, surface hardness and resistance to wear and corrosion. The composition of the implanted layer is not limited by the thermodynamic solubility limits for the implant ions, thus allowing full freedom to implant to the desired concentration. However, the method has certain drawbacks which make it unsuitable for treating the products described above.

1) Ion irradiation is linear, thus making internal coating impossible and complicating the coating of spherical surfaces or the like.
2) The implanted layer is extremely thin—0.1–0.3–$\mu$m—making the method unsuitable for protracted or hard wear.
3) Possible alloying elements remain in the surface.
4) The method is relatively exclusive and expensive since an accelerator is required.

The aim of all the known processes is to achieve better wear properties in titanium or its alloys. The use of titanium and titanium alloys in applications with sliding contact always entails serious tribological problems since poor hardness, adhesive and oxidative properties lead to severe friction and wear problems. An unpredictable increase in friction and wear will often lead to expensive breakdowns. The processes described attempt to solve this problem primarily by increasing the hardness.

SUMMARY OF THE INVENTION

The object of the present invention is to eliminate the inconveniences of the known processes described above. With the process according to the invention a uniformly distributed nitride layer is obtained which also coats internally (e.g. in capillaries). The layer is also characterised by extremely good adhesion, high hardness (at least 2000 $HV_{0.05}$), good friction and wear properties, improved corrosion-proof and biocompatibility properties of the titanium or titanium alloy, and equal or improved biocompatibility properties even for titanium alloys where a depletion of the alloying element is obtained in the nitride layer.

The problem is solved in that the untreated objects are subjected in a vacuum furnace with an atmosphere consisting of pure nitrogen gas, to a temperature of 650°–1000° C. and a pressure below atmospheric pressure, after which the temperature is reduced.

A high gas flow is necessary during heating to the treatment temperature. This is in order to remove contamination layers (contamination layers=a few atom layers with adsorbed carbon and oxygen which exist on all surfaces) and impurities which are desorbed during the heating process, from the surface. This prevents them from reacting with the substrate (titanium or titanium alloy). Such a reaction quickly produces an effective diffusion barrier, thereby preventing the formation of a pure titanium nitride layer of sufficient thickness. Titanium and titanium alloys are particularly sensitive to the above-described effected when the reactivity is very high.

By means of the process according to the present invention a continuous, uniformly distributed nitride is formed having high purity, the thickness of which can be controlled between 0.5 and 10 $\mu$m, depending on the treatment time and temperature.

Titanium reacts with nitrogen gas ($N_2$) and the surface is converted to titanium nitride (TiN) which is an extremely hard coating material, resistant to wear and corrosion and having good friction properties. The method according to the invention also gives extremely good results with titanium alloys.

The most usual titanium alloy is Ti—6Al—4 V (ASTM grade 5). This alloy combines good strength properties (ultimate stress limit, elasticity module, ductility) with good properties from the manufacturing point of view (can be cut and welded, and an extremely smooth finish can be obtained, etc.)

A titanium nitride layer with extremely good adhesion is obtained on the surface by using the method according to the invention for nitration/surface conversion of titanium and titanium alloys. Friction and wear properties are greatly improved. The layer also improves the corrosion properties of titanium and titanium alloys. The alloying elements in Ti—6Al—4 V are depleted in the layer and a pure titanium nitride is obtained since the diffusion of Al and V is inhibited by TiN.

BRIEF DESCRIPTION OF THE DRAWINGS

The invention will be described in more detail with reference to the accompanying drawings in which, FIG. 2 shows pictures taken by Scanning Electron Microscopy (SEM) and Light Miscroscopy (LM) on polished cross sections of nitrated titanium components. The extent of the titanium nitride layer is clearly visible as lighter contrast below the black upper part of the picture. Below the light stripe is the substrate material a) Ti—6Al—4 V treated at 845° C. for 6 hours, SEM picture and b) pure titanium treated at 930° C. for 9 hours, LM picture.

FIG. 3 shows how the process parameterstemperature and time affect the surface finish of nitrated components manufactured from titanium or titanium alloy a) effect of the temperature, treatment time 6 hours, and b) effect of the time, treatment temperture 845° C.

FIG. 4 shows how the process parameters temperature and time affect the thickness of the surface-converted titanium nitride layer for the alloy Ti—6Al—4 V, a) effect of the temperature, treatment time 6 hours, and b) effect of the time, treatment temperture 845° C.

FIG. 5 shows the morphology and surface finish before and after nitration for pure titanium a) before nitration, $R_a=0.005\mu m$, b) after nitration at 845° C. for 6 hours, $R_a=0.12\mu m$, FIG. 6 shows the morphology and surface finish before and after nitration for the alloy Ti—6Al—4 V, a) before nitration, $R_a=0.005\mu m$, b) after nitration at 845° C. for 6 hours, $R_a=0.17m$.

DESCRIPTION OF THE PREFERRED EMBODIMENTS

Figure 1:
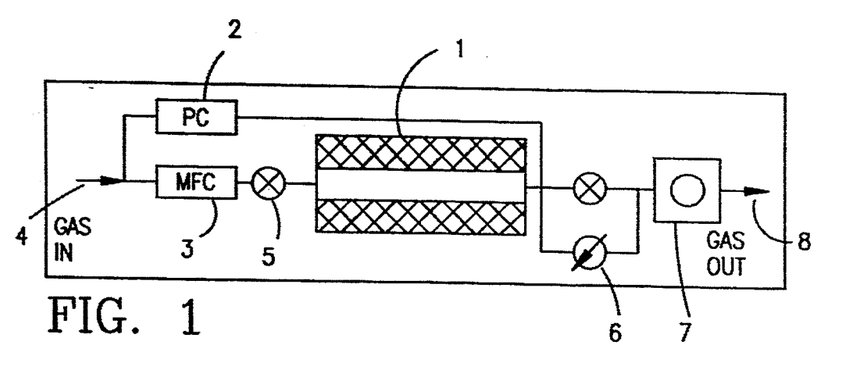
FIG. 1 shows a diagrammatic sketch for a nitration system according to the invention.

According to the invention objects, e.g. joint prostheses, valve components or cylinders, consisting of untreated titanium or titanium alloys, are placed in a vacuum furnace in which pure nitrogen gas 2 passes under control pressure and flow. The pressure in the furnace is below atmospheric pressure and the temperature is maintained at a constant value between 650°–1000° C.

The surface reaction of titanium is diffusion-controlled and thus follows a parabolic velocity law. The nitration rate thus decreases with increasing nitration time. The diffusion rate of titanium decreases with the time when the thickness of the nitride layer increases and the titanium acquires a longer diffusion distance. It is thus obvious that it is impossible to obtain thick layers of nitride. The nitrogen must be extremely pure since impurities would easily react with the reactive titanium or titanium alloy. A diffusion barrier would then be formed which would prevent a nitride layer from being formed.

The most important parameters, such as temperature, time, pressure and gas flow, can be exactly measured, set and controlled, Certain criteria for the surface coating must be fulfilled if the components are to function satisfactorily over a long period of time:

1) Its hardness must be sufficient to prevent any foreign particles from scratching and/or causing fatigue in the surface thereby causing malfunction,
2) Its thickness shall be such that it will withstand wear occurring over a long period of time. However, the surface coating may not be too thick which would incur the risk of cracks or flaking thereby causing malfunction,
3) Friction shall be low in order to prevent wear of the material it comes into contact with,
4) Adhesion shall be sufficient to withstand long usage without risk of the coating flaking off due to surface fatigue.
5) Resistance to corrosion and chemicals shall be sufficient for the intended applications.
6) Biocompatibility shall be acceptable.
7) The nitride shall be free from impurities and alloying elements in order to prevent toxic (allergic) reactions.

Experiments have been performed to determine suitable process parameters for the surface treatment in order to fulfil the above requirements. The following results and experience are directly connected to the above requirement specification.

1) Hardness. The titanium nitride has a hardness ($HV_{0.05}$) of about 2000 Vickers, which is fully sufficient for most applications. By way of comparison it may be mentioned that untreated titanium grade 5 (Ti—6Al—4 V) has $HV_{0.05}=405$ kg/mm$^2$, titanium grade 2 has $HV_{0.005}=260$ kg/mm$^2$, high speed tool steel has $HV_{0.05}=1000$ kg/mm$^2$, and hard metal has $HV_{0.05}=1600$ kg/mm$^2$.

1) Experience from the coating of tool steel shows that a coherent coating with a thickness of 2–4$\mu$ is ideal. The thickness is primarily dependent on treatment time and temperature. The partial vacuum and flow of the gas during treatment are less critical. However, during heating the velocity of the gas flow must be high in order to remove impurities from the surface. These impurities otherwise react with the surface and form a diffusion barrier, resulting in too thin a coating, also containing impurities.

3) To a great extent friction and wear (primarily of the material the component comes into contact with) are a function of the surface finish, which in turn is dependent on treatment time, treatment temperature and type of titanium material. For certain applications some form of finishing process is necessary with nitration, in order to fulfil the requirements. This is preferably a chemo-mechanical method which has been found to give excellent results. A marked improvement of the surface finish guarantees a low wear rate, low friction and thus long life.

4) The adhesion causes no problems since no foreign substances (e.g. salt-forming crystals) are present and since the process achieves a surface conversion, not coating. From the adhesion aspect this gives an ideal intermediary surfaces between titanium and titanium nitride which is formed by chemical reaction between only the nitrogen gas and the titanium.

5) There is no deterioration in the resistance to acid or basic solutions in comparison with titanium. Other chemical-resistance tests were also performed and the substances precipitated out were checked by atom-absorption measurements performed on the liquid. The results were satisfactory.

6) The biocompatibility of titanium nitride is fully acceptable since nitrogen is inert and titanium has been proven to have good properties.

7) Thanks to the high quality of the vacuum system, there is substantially no leakage from the surroundings (less than 25–50 mT/hour). This, together with the heating process described earlier, enables a completely pure nitride to be obtained by the method, without damaging alloying elements, even at nitration of the useful alloy Ti—6Al—4 V.

The following examples show results obtainable by means of the present invention.

EXAMPLES

Figure 2A:
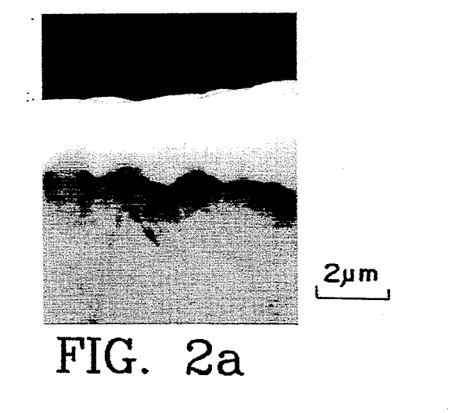
Figure 3A:
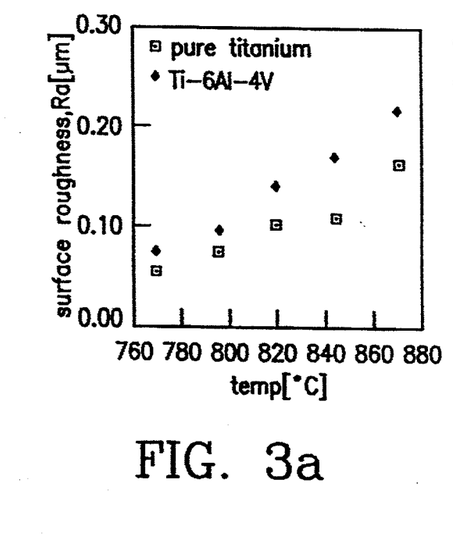
Figure 3B:
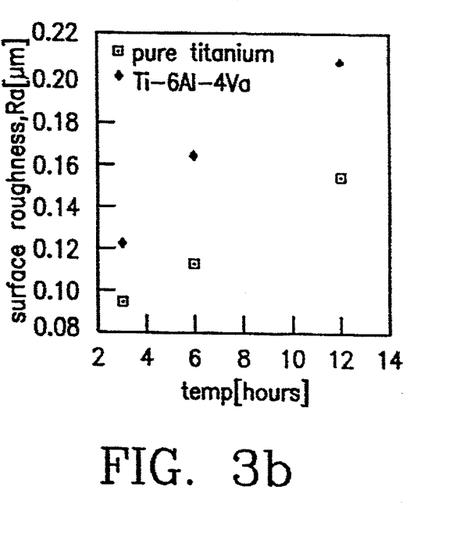
Figure 4A:
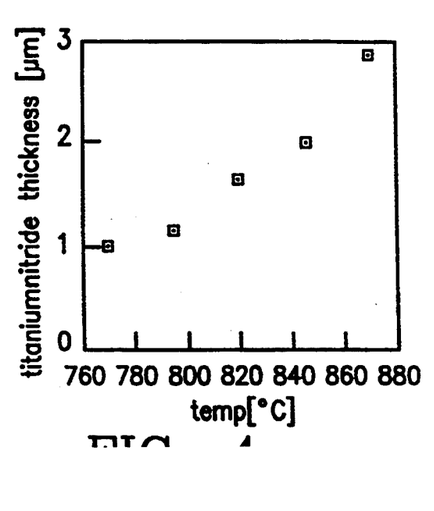
Figure 6A:
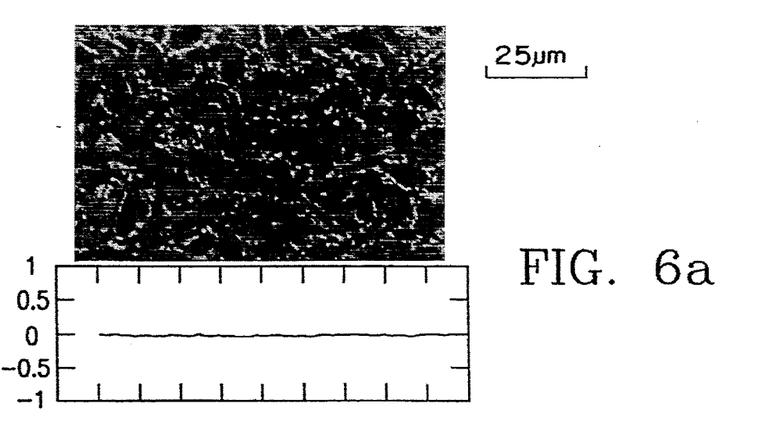
Figure 6B:
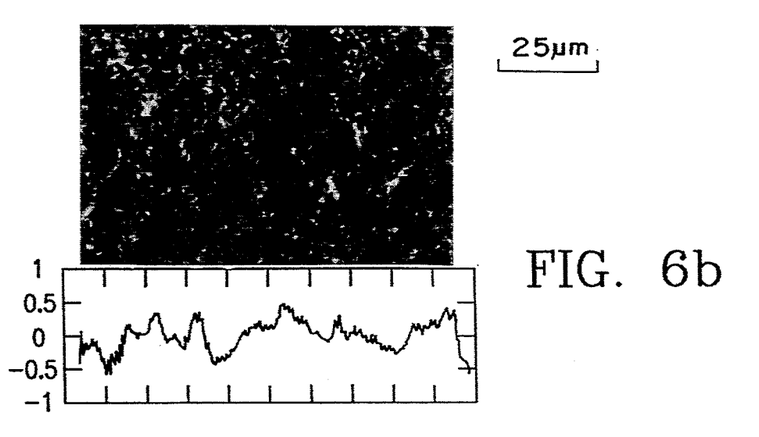
Figure 7:
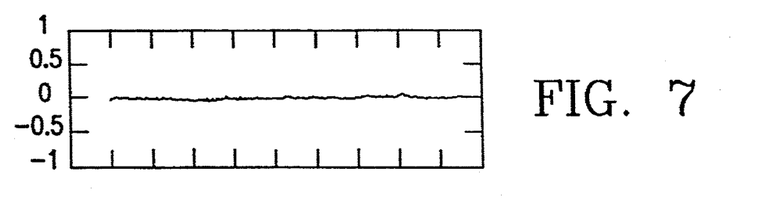
FIG. 7 shows the surface finish after chemo-mechanical polishing of the titanium nitride layer, $R_a=0.008\mu m$.
Figure 8:
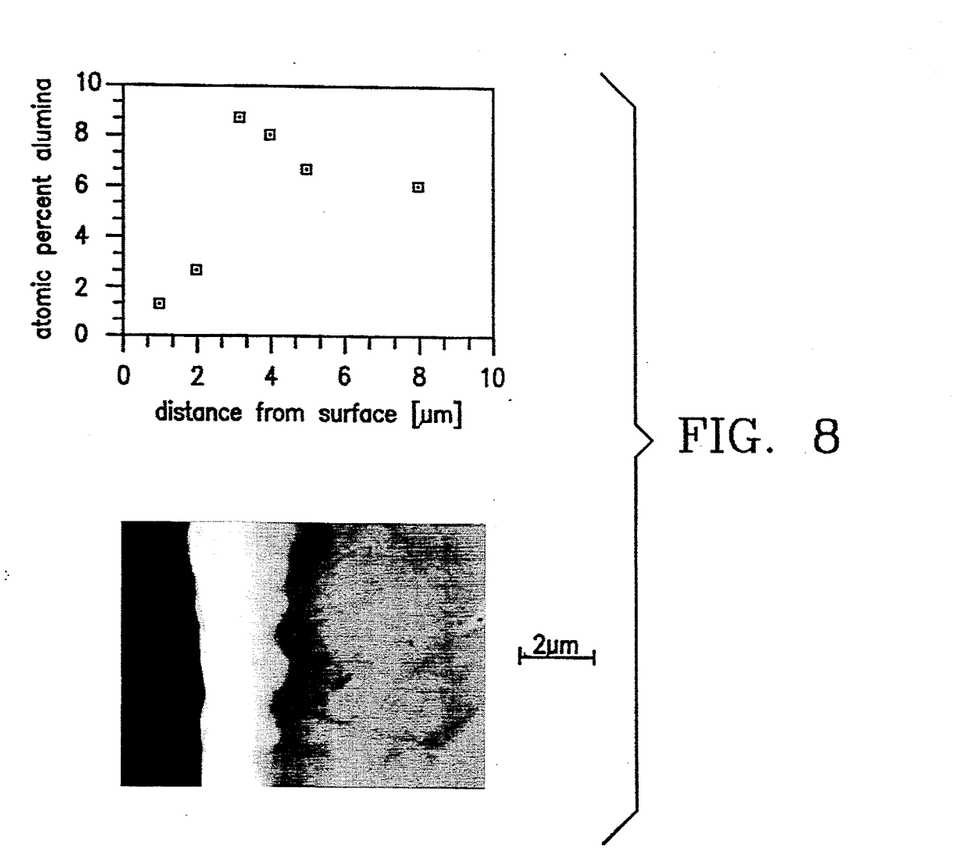
FIG. 8 shows how the alloying element aluminium is depleted in the titanium nitride layer when treating the alloy Ti—6Al—4 V. Equivalent depletion is also obtained for vanadium and a pure nitride is thus formed. The technique used is energy-dispersive spectroscopy (EDS). Process parameters: 845° C., 6 hours.

1. A flat titanium component 3 of the alloy T—6Al—4 V was subjected for 6 hours to a nitrogen gas flow of 80 SSCM, a pressure of 400 hPa and a temperature of 845° C. in a furnace according to FIG. 1. A titanium nitride layer 4 having a thickness of 2$\mu$m, (see FIGS. 2a and 4a) hardness 2000 $HV_{0.05}$ and surface finish $R_a = 0.17\mu$m (see FIGS. 3a and 6b) was formed on the surface. After polishing, a nitride layer having a surface finish $R_a = 0.008$ $\mu$m (see FIG. 7) was obtained. This nitride layer was also depleted of the alloying substances aluminium and vanadium (see FIG. 8).

Figure 2B:
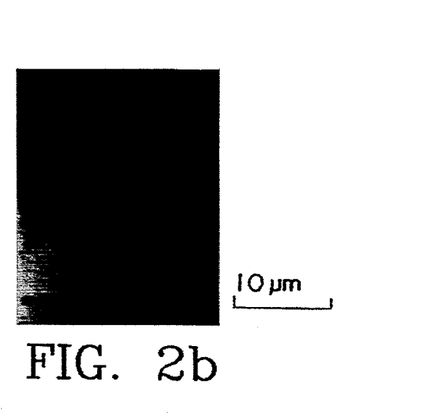

2. A pipe of the alloy T—6Al4 V was subjected for 9 hours to a nitrogen gas flow of 80 SSCM, a pressure of 400 hPa and a temperature of 930° C. in a furnace according to FIG. 1. A titanium nitride layer having a thickness of 5.4 $\mu$m and hardness of 2000 $HV_{0.05}$ was formed on the surface (see FIG. 2b). After polishing, the nitride layer fulfilled the surface finish requirements specified above, (see FIG. 7) and was also depleted of Al (see FIG. 8).

3. Flat titanium sheets treated by means of nitritation and also coated with titanium nitride using the physical vapour deposition (PVD) technique, were tested by repeated turning against flat seals of hard teflon plastic (PEK). The seals were operating under a pressure of 250 bar and the leakage was utilized as a gauge of the function of the seal. The titanium sheets coated with titanium nitride according to the PVD technique functioned satisfactorily for about 2000 cycles, after which they malfunctioned due to the coating flaking off. The titanium sheets which had been surface-converted by means of nitration were still functioning satisfactorily after 140,000 cycles.

Figure 4B:
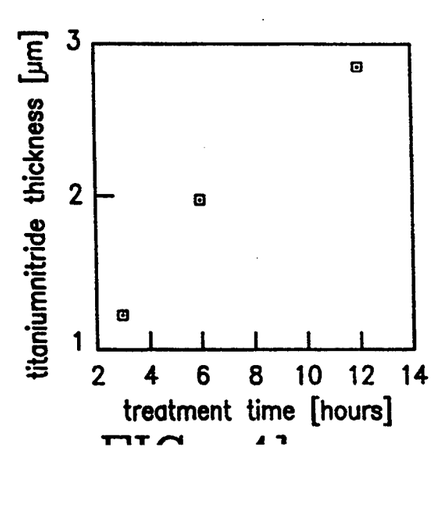
Figure 5A:
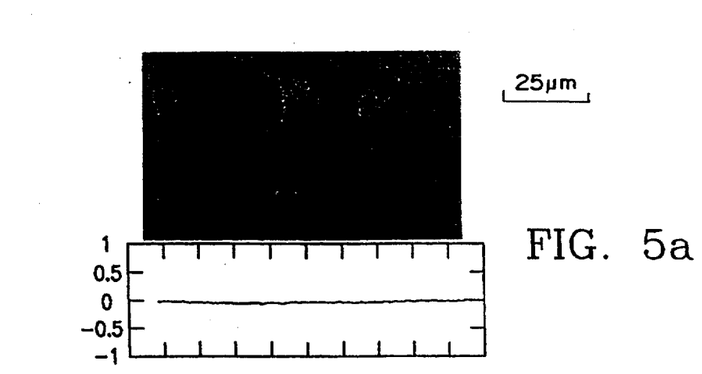
Figure 5B:
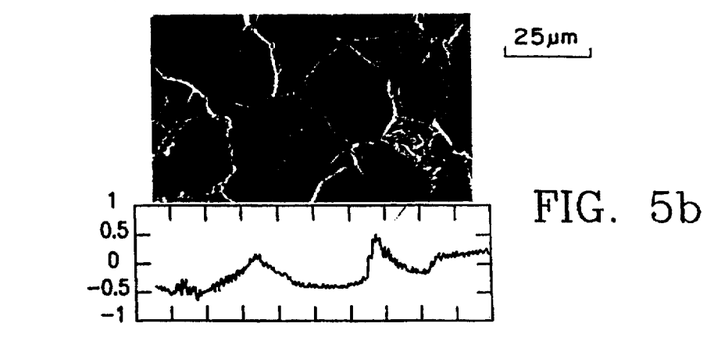

4. A cylinder piston was geometry-tested. The piston was made of teflon and the cylinders were treated by oxidation, anodization and nitration. Untreated cylinders were also tested. The untreated cylinders and anodized cylinders malfunctioned almost immediately due to cutting. The oxidized cylinders in some cases functioned satisfactorily for a considerable time with good sealing and low wear, whereas in other cases they malfunctioned at an early stage. This may be explained by the poor mechanical stability and negligible hardness of the thin oxide layer. The nitride obtained with the nitration process described above function perfectly reliably over a long period of time if it was pre-polished (see FIG. 4) in order to avoid wear on the relatively soft seal. This surface never malfunctioned.

A new vacuum system for nitration has been constructed. In FIG. 1, 1 designates a furnace+furnace tube, 2 pressure control, 3 mass flow control, 4 gas entering, 5 valve, 6 needle valve, 7 vacuum pump and 8 gas leaving. The central part of the system is the furnace 1 which in fact consists of three part-furnaces and six heating elements. This is in order to obtain a long and uniform temperature profile. The temperature varies by at most seven degrees within a length of 50 cm and 3 degrees within a length of 30 cm. A uniform temperature profile is necessary in order to avoid variations in the thickness of the titanium nitride layer. A long heating zone is also important so that the gas phase can be activated before coating occurs.

The temperature control occurs automatically and each furnace part can be controlled independently of the other two. The desired temperature is set with the aid of control units, thermoelements sensing the temperature, which is then controlled by thyristors. Pressure and gas flow are also controlled automatically after setting. The pressure is set by means of a needle valve 6, to just below the desired temperature. The pressure control then regulates the gas pressure by dosing a sufficient quantity of gas 4.

The furnace tube consists of quartz glass and has a diameter of 80 mm and length of about 110 cm. Quartz glass will withstand temperatures up to about 1100° C. The rest of the equipment consists of stainless steel except for the end connections to the furnace tube, which are made of aluminium. Water-cooling is required to protect these end connections from the heat radiating from the furnace.

The equipment must fulfil the highest tightness requirements. With the volume mentioned above, the leakage rate may not exceed about 50 millitorr/hour if the surface-converted layer is to obtain high purity, hardness and adhesion. Other mechanical properties of the layer may also be adversely affected if any leakage occurs. (A more brittle layer, poorer resistance to fatique and higher friction may be obtained, for instance.)

The material according to the invention is suitable for joint prostheses. Thanks to the unique biocompatibility properties of titanium (fuses with bone marrow, no precipitation caused by exposure to body liquids) it is an extremely suitable material for use in joint prostheses (it is also currently used for this purpose). To obtain the requisite stength the alloy Ti—6Al1.4 V must be used. This alloy is also easier to work. However, from the biological point of view, it is inadvisable to expose body liquids or bone marrow to alloys containing Al since this may easily result in toxic (allergic) reactions after protracted use, and the body will then reject the prosthesis. The method according to the invention for surface conversion of titanium and titanium alloys gives strong depletion of the alloying elements in the surface-converted layer and pure titanium nitride is obtained. The undesired effect obtained due to the presence of Al is thus eliminated. Furthermore, the corrosion properties of TiN exceed even those of titanium. The good friction and wear properties of TiN have also been documented. Thanks to the invention, therefore, properties sufficient mechanical strength (ultimate stress limit, E-module, ductility), desired corrosion and biocompatibility properties, as well as requisite tribological properties (wear, friction) have been combined for the joint-prosthesis application.

The method according to the invention also enables Ti—6Al4 V to be used in valve components and pump cylinders.

Valve and pump components made of titanium and titanium alloys are often used in the biotechnical and chemical industries. The problem of uncontrolled friction and wear properties is equivalent here to that in joint prostheses. From the strength aspect it is often possible to use Ti. However, problems arise in machining this material—turning, milling and especially finishing the surface. The alloy Ti—6Al—4 V, on the other hand, is considerably easier to machine and thus also to obtain a reasonable surface finish, thereby creating the conditions for obtaining a surface which, from the friction, wear and sealing aspects, is necessary in order to avoid leakage and malfunction. In this case also Al is an undesired element from the corrosion aspect (precipitation). A titanium nitride layer according to the invention combines mouldability and machinability with excellent friction, wear and corrosion properties.

We claim:

1. Articles comprising joint prostheses, prothesis shafts, wear-parts for prosthesis shafts, hip and knee joints, valve parts or pump cylinders formed of titanium and titanium alloys and having a surface conversion layer consisting of an integral continuous uniformly distributed, hard, wear-resistant and pure titanium nitride layer of between 0.5 and 10 μm having a hardness of at least 2000 $hV_{0.05}$.

2. Articles as claimed in claim 1, wherein the pure titanium nitride layer is between 2 and 4 μm.

3. Articles as claimed in claim 1, wherein the surface is finished to high surface fineness using a chemo-mechanical polishing method.

4. Articles as claimed in claim 2, wherein the surface is finished to high surface fineness using a chemo-mechanical polishing method.

* * * * *

UNITED STATES PATENT AND TRADEMARK OFFICE
CERTIFICATE OF CORRECTION

PATENT NO. : 5,427,631
DATED : June 27, 1995
INVENTOR(S) : ERIK JOHANSSON et al.

It is certified that error appears in the above-identified patent and that said Letters Patent is hereby corrected as shown below:

In the drawings, Sheet 2 of 4 should be deleted and substitute therefor the attached Sheet 2 of 4.

Signed and Sealed this

Twentieth Day of July, 1999

Attest:

Q. TODD DICKINSON

Attesting Officer

Acting Commissioner of Patents and Trademarks